Figure 1:
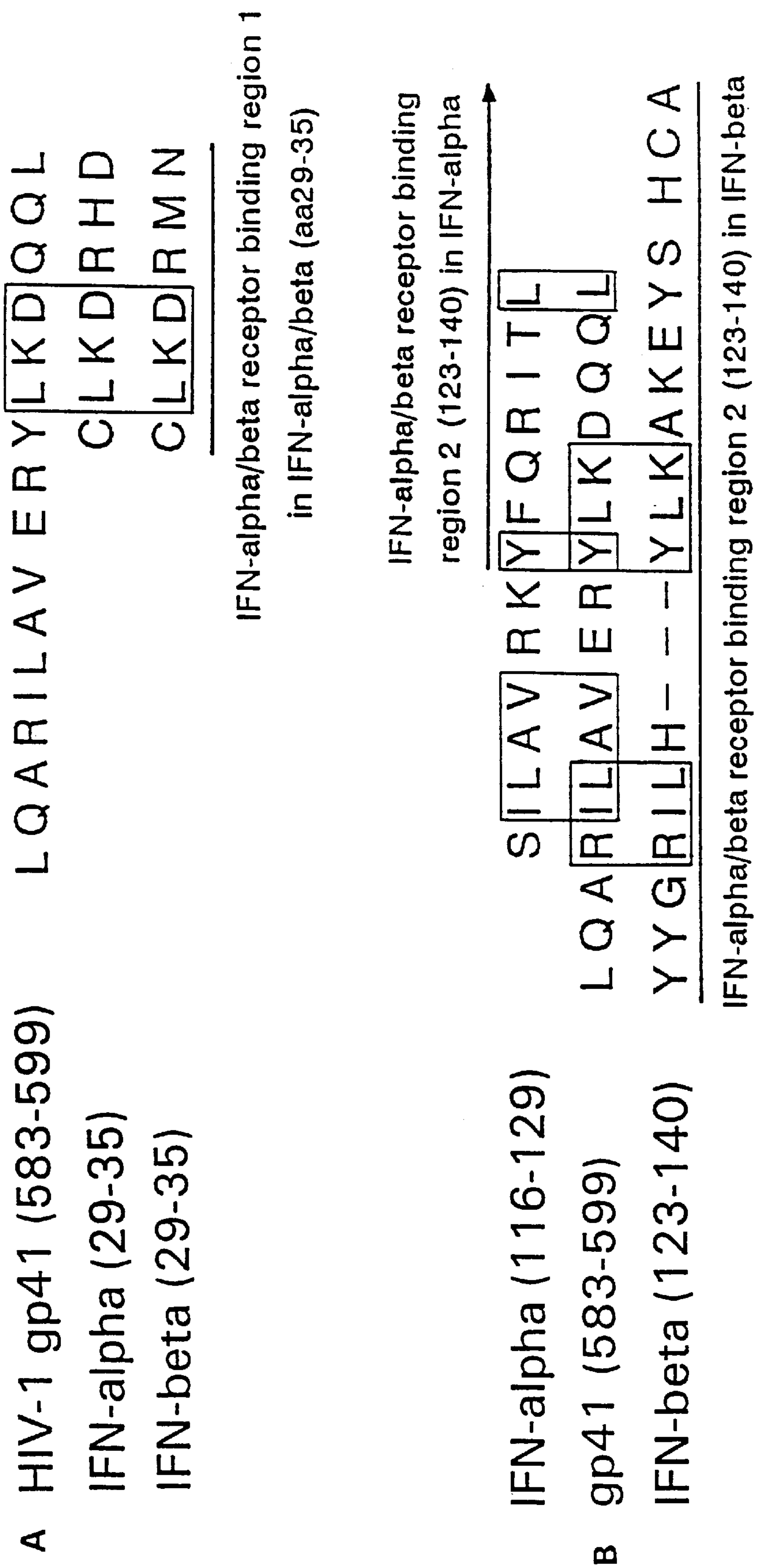

US006140043A

United States Patent [19]

Dierich et al.

[11] Patent Number: 6,140,043

[45] Date of Patent: Oct. 31, 2000

[54] PHARMACEUTICAL COMPOSITIONS FOR COMPETITIVELY INHIBITING THE BINDING OF A RETROVIRUS TO THE IFN-RECEPTOR AND MEANS FOR DIAGNOSIS OF AN HIV INFECTION

[75] Inventors: Manfred P. Dierich, Innsbruck, Austria; Ying-Hua Chen, Beijing, China

[73] Assignee: Rentschler Biotechnologie GmbH, Laupheim, Germany

[21] Appl. No.: 09/029,052

[22] PCT Filed: Aug. 19, 1996

[86] PCT No.: PCT/EP96/03648

§ 371 Date: Apr. 20, 1998

§ 102(e) Date: Apr. 20, 1998

[87] PCT Pub. No.: WO97/06818

PCT Pub. Date: Feb. 27, 1997

[30] Foreign Application Priority Data

| | | | |
|---|---|---|---|
| Aug. 18, 1995 | [EP] | European Pat. Off. | 95113036 |
| Oct. 10, 1995 | [EP] | European Pat. Off. | 95115970 |

[51] Int. Cl.[7] .............................. C12Q 1/70; C12N 5/06; A61K 39/40; A61K 39/42; C07K 16/00

[52] U.S. Cl. .......................... 435/5; 435/335; 435/339.1; 424/148.1; 424/160.1; 424/208.1; 530/388.35; 530/388.22; 530/389.4

[58] Field of Search ........................... 435/5, 335, 339.1; 424/148.1, 160.1, 208.1; 530/388.35, 388.22, 389.4

*Primary Examiner*—Hankyel Park

*Attorney, Agent, or Firm*—Birch, Stewart, Kolasch & Birch, LLP

[57] ABSTRACT

The present invention is based on the observation that HIV does not only interact with the CD4 receptor of target cells but that there exists a different type of interaction between HIV envelope protein and the IFN receptor of the target cell. Thus, blocking such interaction can be useful for preventing or treating retroviral infections. Accordingly, the present invention relates to pharmaceutical compositions for competitively inhibiting the binding of a retrovirus, preferably HIV, to the IFN-receptor of a target cell. Preferably, said pharmaceutical compositions comprise a protein, polypeptide or equivalent molecule or a combination thereof which binds to the IFN-α/β-receptor or to HIV-gp41. Furthermore, the present invention relates to the use of said protein, polypeptide or equivalent molecule or IFN-β or a combination thereof for the preparation of a pharmaceutical composition for preventing or treating retroviral infections. The present invention also relates to a combination of substances for the diagnosis of an HIV infection which is based on the detection of the interaction between HIV-gp41 and the IFN-α/β-receptor.

30 Claims, 11 Drawing Sheets

A   HIV-1 gp41 (583-599)    L Q A R I L A V E R Y L K D Q Q L
    IFN-alpha (29-35)                           C L K D R H D
    IFN-beta (29-35)                            C L K D R M N IFN-alpha/beta receptor binding region 1 in IFN-alpha/be

PHARMACEUTICAL COMPOSITIONS FOR COMPETITIVELY INHIBITING THE BINDING OF A RETROVIRUS TO THE IFN-RECEPTOR AND MEANS FOR DIAGNOSIS OF AN HIV INFECTION

This application is the national phase under 35 U.S.C. §371 of prior PCT International Application No. PCT/EP 96/03648 which has an International filing date of Aug. 19, 1996 which designated the United States of America, the entire contents of which are hereby incorporated by reference.

The present invention relates to pharmaceutical compositions for competitively inhibiting the binding of a retrovirus, preferably HIV, to the IFN-receptor of a target cell. Preferably, said pharmaceutical compositions comprise a protein, polypeptide or equivalent molecule or a combination thereof which binds to the IFN-α/β-receptor or to HIV-gp41. Furthermore, the present invention relates to the use of said protein, polypeptide or equivalent molecule or IFN-β or a combination thereof for the preparation of a pharmaceutical composition for preventing or treating retroviral infections. The present invention also relates to a combination of substances for the diagnosis of a HIV infection which is based on the detection of the interaction between HIV-gp41 and the IFN-α/β-receptor.

Since the discovery of the human immunodeficiency virus (HIV) as the etiological agent of AIDS, there have been many advancements in the understanding of the replicative cycle of HIV and in the design of antiviral drugs. The development and application of such antiviral pharmaceutical compositions that inhibit the replication of HIV are based on the knowledge of the replicative cycle of HIV: The first step in HIV replication is access of the retrovirus to the organism through exposure to HIV-infected blood or body fluids. The envelope glycoprotein gp120 which plays a major role, selectively binds to it's receptor CD4, a cell-surface protein located on a subpopulation of helper T lymphocytes. After binding, the HIV virus enters the susceptible cells. The virus is uncoated within the cytoplasm of these cells yielding viral genomic RNA which is transcribed by virus-encoded reverse transcriptase into single-stranded DNA. Then, this single-stranded DNA is duplicated, and, after degradation of the RNA strand by ribonuclease H, proviral (unintegrated) circular double stranded DNA is formed. The proviral DNA can then migrate into the nucleus of the host cell and become integrated into the genome. After a latency period RNA polymerases of the host cell transcribe the DNA of the integrated HIV into mRNA, which is then translated into viral proteins. After translation the precursor proteins are further modified (specific cleavage by virus-specific proteins and glycosylation by host enzymes) and the viral proteins are assembled in the cytoplasm. After budding of the virus from the host cell surface additional cells are infected and the cycle is repeated.

Known targets in the replicative cycle of HIV for therapeutic intervention include binding of the target cell and entry (previous agents: soluble CD4, SCD4-PE40), reverse transcription of the retrovirus (inhibitors: Zidovudine, Nevirapine etc.), transcription and translation (inhibitors: Trichosanthin, tat-antagonists, anti-sense oligonucleotides etc.) and viral maturation and budding (inhibitors: N-butyl-DNJ, protease inhibitors).

Furthermore, interferons (IFN) are used for therapeutic intervention of HIV infection, since they interact on different levels of the HIV replication cycle (reviewed in Pitha, Antiviral Res. 24 (1994), 205–219).

However, although progress has been made in developing drugs and therapies for treating, retroviral, for example, HIV infections, effective pharmaceutical compositions without severe side effects are still lacking.

Thus, the technical problem underlying the present invention is to provide new compounds for the prevention, treatment and diagnosis of retroviral, preferably HIV, infections which overcome the disadvantages of the prior art compounds.

The solution to said technical problem is achieved by providing the embodiments characterised in the claims. It has been, surprisingly, found that a retrovirus does not only interact with the CD4 receptor of target cells but that there exists a different type of interaction, namely between the IFN-receptor of the target cell and retroviral envelope protein(s) which seems to be independent of the CD4-interaction. Thus, HIV should be able to enter and infect every cell type, since IFN receptors are located on all cells. Accordingly, the present invention relates to a pharmaceutical composition, comprising a protein, peptide or a functionally equivalent molecule or a combination thereof which competitively inhibits the binding of a retrovirus to the IFN-receptor of a target cell and optionally a pharmaceutically acceptable carrier.

In this context, the term "functionally equivalent molecule" refers to any molecule, which is useful as a competitive inhibitor in order to prevent or at least reduce interactions between the IFN-receptor and the retrovirus. Such "functionally equivalent molecules" include, for example any other IFN- or HIV-gp41-binding molecule of peptidic or nonpeptidic character, e.g. any molecule developed by conventional drug design methods according to the basic principles of binding interactions. The term "competitively inhibits", as used herein, relates to any molecular interaction that competitively inhibits the binding of a retrovirus to the IFN-receptor of the target cell, for example, by binding to the receptor, binding to the responsible surface protein of the retrovirus, by receptor independent binding to the target cell, by binding to other sections of the virus surface, by altering the receptor or by altering the responsible surface protein of the retrovirus.

IFN receptors are described in detail in the following publications: Mariano et al. in: Interferon: Principles and Medical Applications, Baron et al. (eds.) UTMB, Galveston, Tex. 1992 pp. 128–138; Schreiber et al., Int. J. Immunopharmacology 14 (1992), 413–419; Uzé et al., J. Interferon Cytokine Res. 15 (1995), 3–26.

The human immunodeficiency virus type 1 (HIV-1) after binding by the envelope protein gp120 to its cellular receptor CD4, enters susceptible cells. Several studies have indicated that this gp120-CD4 interaction alone is not sufficient, but that other cellular receptors for viral entry are needed (reviewed in Levy et al., Microbial. Reviews 57 (1993), 183–289). Several studies, including inhibition of cell fusion by antibodies (Vanini et al., AIDS 7 (1993), 167–174), peptides (Jiang et al., Nature (London) 365 (1993), 113) and mutation of different sites in gp41 (Cao et al., J. Virol. 67 (1993), 2747–2755) have indicated that HIV-1 gp41 plays an important role in virus uptake and more general in AIDS pathogenicity. From these studies two regions in addition to the N-terminal aa517–527 have turned out to be of particular importance for cell fusion and viral uptake, namely aa583–599 and aa650–675. Antibodies against regions in SIV gp32 homologous to both regions in HIV-1 gp41 could protect macaques from SIV-infection (Shafferman et al., PNAS USA 88 (1991), 7126–7130, and Lewis et al., Vaccine 11 (1993), 1347–1355). The first region in gp41 (aa583–599) was demonstrated as immunosuppressive domain (IS-domain) (Ciancioto et al., Immunol. Lett. 19 (1988), 7–14).

The present invention is based on the following observations. Previous studies demonstrated that HIV-1 gp41 independently of CD4, could bind to human T and B cells and monocytes. Thus, it was concluded that in general the target cells (B- and T- cells, monocytes/macrophages) possess, beside CD4, a second receptor on the cell surface which is responsible for the CD4-independent infection of the cell by the retrovirus. Based on findings of the present inventors that gp41 modified MHC antigen expression on these cells and inhibited T cell proliferation, effects similarly shown by human IFN-α and β, but not γ, in the present invention amino acid sequences of gp41 and IFNs were compared and it was surprisingly found that aa586–596 in gp41 showed sequence similarity with human IFN-α/β receptor binding site in IFN-α and IFN-β. Furthermore, a polyclonal antibody raised to human-IFN-β could recognise rsgp41 (recombinant soluble glycoprotein 41) from two different sources and its immunosuppressive peptide (ISP, aa583–599) and inhibit, if preincubated with rsgp41, binding of rsgp41 to human cells completely. Human IFN-β could partially inhibit the binding of rsgp41 to human U937 and Raji cells, but this binding could not be inhibited by IFN-α and IFN-γ. of the gp41 binding proteins isolated by absorption onto gp41-sepharose four proteins were recognised by binding of IFN-β or by a rabbit anti human IFN-α/β receptor antibody by Western blot analysis. Absorbing Raji cell solutes on an IFN-β and IFN-α/β-receptor antibody recognised and bound two cellular proteins of 45 and 50 kDa which were identified as IFN-α/β-receptor proteins; rsg41 and IFN-β could also recognise two additional proteins of 37 and 62 kDa. Furthermore, anti-human IFN-α/β-receptor-antibodies were able to inhibit HIV infection of PBMC (peripheral blood mononuclear cells). These results indicated that amino acid sequence homology of the receptor binding regions in gp41 and human IFN-β results in binding to the same cellular proteins and consequently similar functional activity. Thus, the IFN-α/β-receptor may serve as second cellular HIV receptor for gp41 binding and inhibiting the interaction between the IFN-α/β-receptor and the envelope protein of a retrovirus which binds to said receptor, can thus serve as a novel therapeutic approach for preventing or at least reducing retrovirus infectivity or further propagation of the retrovirus in vivo.

The pharmaceutical compositions comprising the substances of the invention for inhibiting the above discussed interaction can optionally comprise a pharmaceutically acceptable carrier or excipient. Examples of suitable pharmaceutically acceptable carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g. by intravenous, intraperetoneal, subcutaneous, intramuscular, topical or intradermal administration.

In a preferred embodiment of the pharmaceutical composition of the present invention the receptor is the IFN-α/β-receptor.

In another preferred embodiment, the retrovirus is HIV.

In principle, the interaction between the retrovirus and the IFN-receptor can be eliminated by two different approaches, namely by blocking those domains of the IFN-receptor that are responsible for the binding of retrovirus or, vice versa, by blocking those domains of the retroviral envelope proteins that are responsible for binding to the IFN-receptor.

Accordingly, in a further preferred embodiment the pharmaceutical composition of the present invention comprises a protein, peptide or a functionally equivalent molecule or a combination thereof which binds to the IFN-α/β-receptor. Alternatively, the pharmaceutical composition of the present invention comprises a protein, peptide or a functionally similar molecule or a combination thereof which binds to gp41 of HIV. Such substances can be selected by the person skilled in the art by well known methods, for example by blotting, affinity chromatography, other binding techniques etc.

In a still further embodiment the pharmaceutical composition comprises a protein or peptide, which is HIV-gp41, an anti-IFN-α/β-receptor-antibody or a fragment thereof containing an HIV-gp41 receptor binding site (epitope), or IFN-α or IFN-β or a fragment thereof containing the IFN-α/β-receptor binding site (epitope).

HIV-gp41 can be, for example, recombinantly prepared from clone BH10, described by Vornhagen et al., Biotest Bulletin 4 (1990), 91–96. Anti-IFN-α/β-receptor antibodies can be prepared by well known methods using the purified IFN-α/β-receptor as antigen or obtained from Santa Cruz Biotechnology, Inc., California, USA. Monoclonal antibodies can be prepared, for example, by the techniques as described in Köhler and Milstein, Nature 256 (1975), 495, and Galfrè, Meth. Enzymol. 73 (1981), 3, which comprise the fusion of mouse myeloma cells to spleen cells derived from immunised mammals. Fragments comprising an HIV-gp41-receptor binding site (epitope) can be also generated by conventional techniques, for example as described by Bogulawski et al., J. Immunol. Meth. 120 (1983), 51, and Weir (Ed.), Handbook of Experimental Immunology, Blackwell, Edinburgh, 1986.

IFN-α or IFN-β can be obtained, for example, by Rentschler Biotechnology (Laupheim, Germany) and corresponding fragments still comprising an IFN-α/β-receptor binding site (epitope) can be prepared by well known techniques, e.g. enzymatic cleavage, recombinant DNA technology etc.

In an alternative embodiment, the pharmaceutical composition of the present invention comprises a soluble IFN-α/β-receptor, an anti-IFN-β-antibody, an anti HIV-gp41-antibody or a fragment of said proteins or peptides, which contains an HIV-gp41-binding site (epitope). Antibodies and fragments which still bind HIV-gp41 can be obtained by the methods described above or, for example, from Biosource International (California, USA). A soluble IFN-α/β receptor species can be created using generally known recombinant DNA-techniques and using already published data about the IFN-α/β receptor gene. Omitting the gene(s) segments which enclose the transmembrane and intracellular receptor domains for instance by using polymerase chain reaction (PCR) technology results in an artificially shortened receptor gene. This shortened receptor gene still encodes the ligand binding extracellular and therefore soluble receptor domain. Expressing it in an appropriate system leads to a soluble IFN-α/β receptor.

In a particularly preferred embodiment, the pharmaceutical composition comprises at least two proteins or peptides binding to the IFN-α/β-receptor or to HIV-gp41 or a combination containing at least one of the IFN-α/β-receptor binding proteins or peptides and at least one of the HIV-gp41 binding proteins. Useful combinations which may have additive or synergistic effects and/or lead to a reduction of possible side effects can be developed by the person skilled in the art by routine testing. The amount to be administered will depend on the route of administration, the severity of the infection, the condition of the patient etc.

In a further preferred embodiment, the pharmaceutical composition of the present invention can be used for the prevention or treatment of a retroviral infection, preferably an HIV-infection.

In a still further preferred embodiment, the pharmaceutical composition additionally comprises an anti-viral drug. Such a combination may further enhance the effectiveness of said compositions and/or reduce undesired side effects. Examples of suitable anti-viral drugs are described e.g. by Flechter, Am.J.Hosp.Pharm. 51 (1994), 2251–2267, or by Stein et al., Clin.Inf.Dis. 17 (1993), 749–771.

Additionally, the pharmaceutical compositions of the present invention may contain a ligand for CD4 or a ligand for gp120 surface protein of HIV. Such a combination may further increase the potency of said compositions, since they inhibit the interaction of the retrovirus with such target cells exhibiting CD4 on their surface on two different routes. Examples of suitable CD4-ligands include gp120 or fragments thereof comprising a binding site for CD4.

A further object of the present invention is the use of the above proteins, peptides or functionally equivalent molecules for the preparation of a pharmaceutical composition for the prevention or the treatment of a retroviral infection, preferably an HIV-infection. A preferred embodiment relates to the use of said proteins, peptides or functionally equivalent molecules in combination with an anti-retroviral drug and/or a ligand for CD4.

A still further object of the present invention is the use of IFN-β or a molecule having an analogous effect for the preparation of a pharmaceutical composition for the prevention or treatment of a retroviral infection by application of a high dose, which is suitable for the systemic treatment. For such novel use of IFN-β in general doses in the range of 0.1–1.0x$10^6$ International Units (IU) per kg body weight are required. However, the appropriate amounts of IFN-β may vary depending on the particular conditions. Substances that are analogous to IFN-β with respect to the binding to the IFN-α/β-receptor can be determined by blotting, affinity chromatography, or other binding techniques and include IFN-β fragments, peptides or other designed molecules recognized by the IFN-α/β receptor.

Finally, the present invention relates to the combination of substances for the diagnoses of a HIV infection, based on the detection of the interaction between HIV-gp41 and the IFN-α/β-receptor.

For instance, a diagnostic procedure to detect HIV infection by detection of gp41 surface protein could be established as a “sandwich system” as follows: A basic layer of IFN-α/β-receptor is able to bind HIV-derived gp41. Bound gp41 is a target for a specific, radioactively labelled or dye- or enzyme-coupled antibody (or antibody fragment) permitting a sensitive detection of gp41.

LEGENDS TO THE FIGURES

FIG. 1: Amino acid sequence similarity between HIV-1 gp41 and human IFN-Á and IFN-β receptor binding sites.

A, sequence homology between the first binding site of $gp41_{IIIB}$ (aa583–599, SEQ ID NO: 1) and the IFN-α/β receptor binding region 1 of IFN-α (SEQ ID NO: 2) and IFN-β (SEQ ID NO: 3) (aa29–35); B, sequence homology between the first binding site of $gp41_{IIIB}$ (SEQ ID NO: 1) and the IFN-α/β receptor binding region 2 of IFN-α (SEQ ID NO: 4) and IFN-β (SEQ ID NO: 5) (aa123–140).

Figure 2:
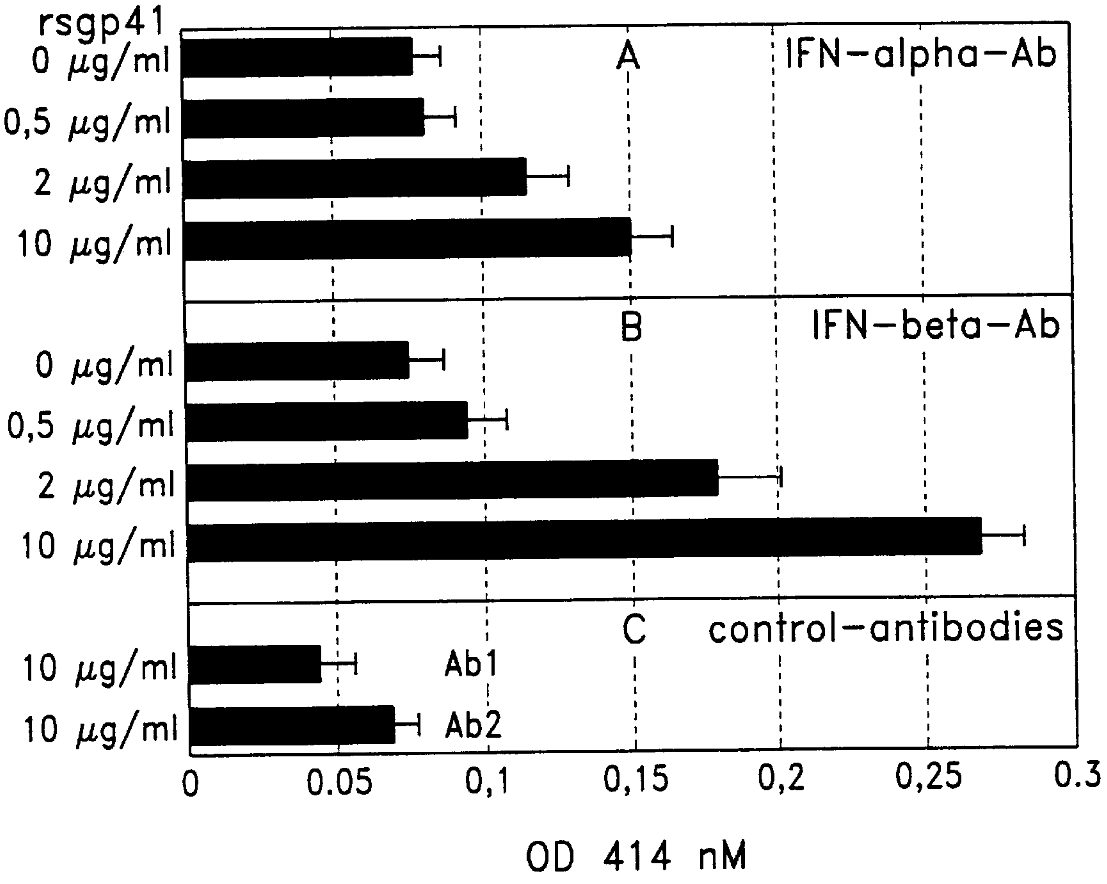

FIG. 2: Polyclonal sheep antibodies to human IFN-Á and IFN-β dose-dependently recognised rsgp41 in an ELISA-assay.

A, polyclonal sheep anti-huIFN-α antibody (immunoglobulin) (4x$10^3$ NU/ml) binding to rsgp41; B, Polyclonal sheep anti-huIFN-β antibody (immunoglobulin) (4x$10^3$ NU/ml) binding to rsgp41; C, two control antibodies binding to rsgp41 (Ab1: sheep immunoglobulin to human factor I, 1:10, Ab2: normal sheep immunoglobulin, 10 μg/ml).

Figure 3:
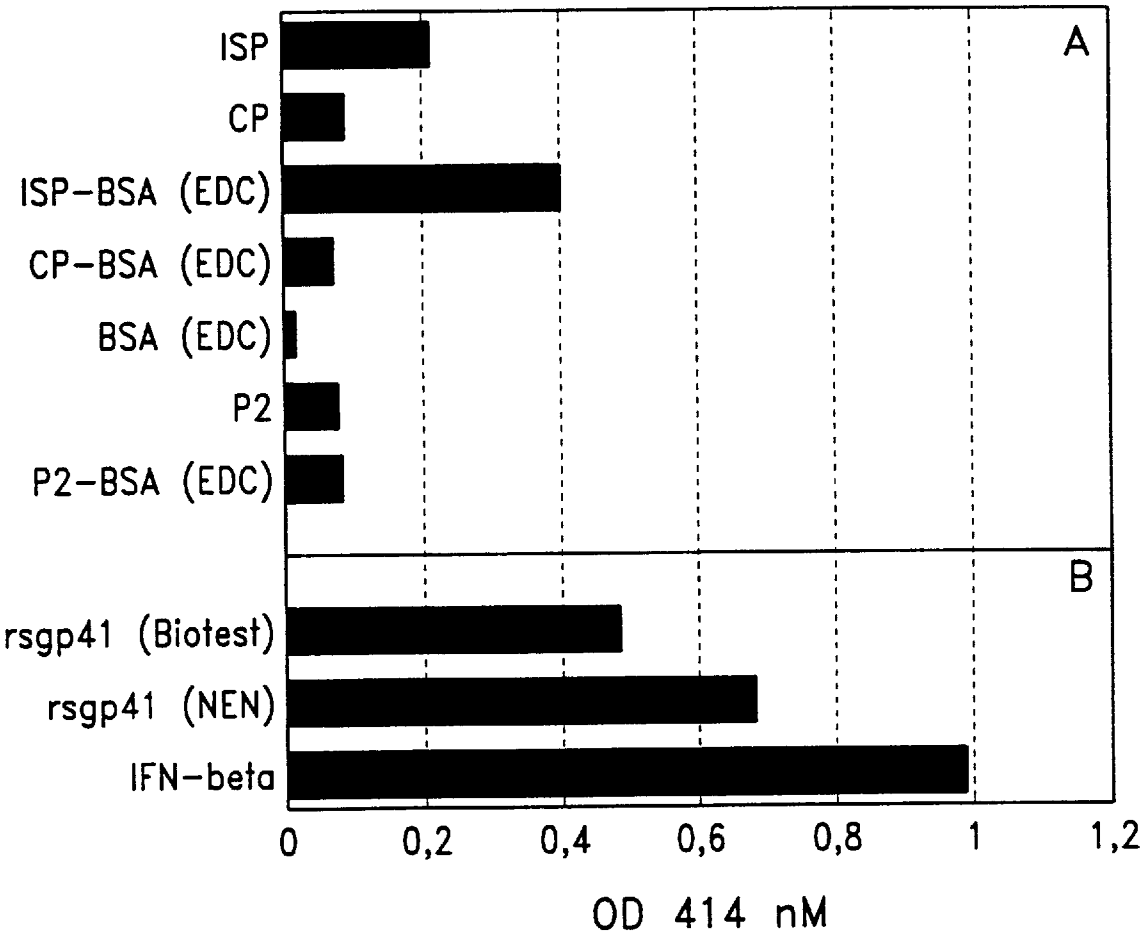

FIG. 3: Polyclonal sheep anti-human IFN-β antibody recognised gp41 IS-peptide (ISP) and two rsgp41 in an ELISA-assay.

A, anti-huIFN-β antibody (immunoglobulin) (4x$10^3$ NU/ml) binding to ISP, P2, CP (control peptide) and their BSA-conjugates as well as EDC-treated carrier protein (BSA/EDC); B, anti-huIFN-β antibody (4x$10^3$ NU/ml) binding to two rsgp41 (aa539–684) from Biotest, Germany; aa567–684 from NEN, USA) (10 μg/mg) and human IFN-β (2x$10^5$ U/ml=600 μg/ml).

Figure 4A:
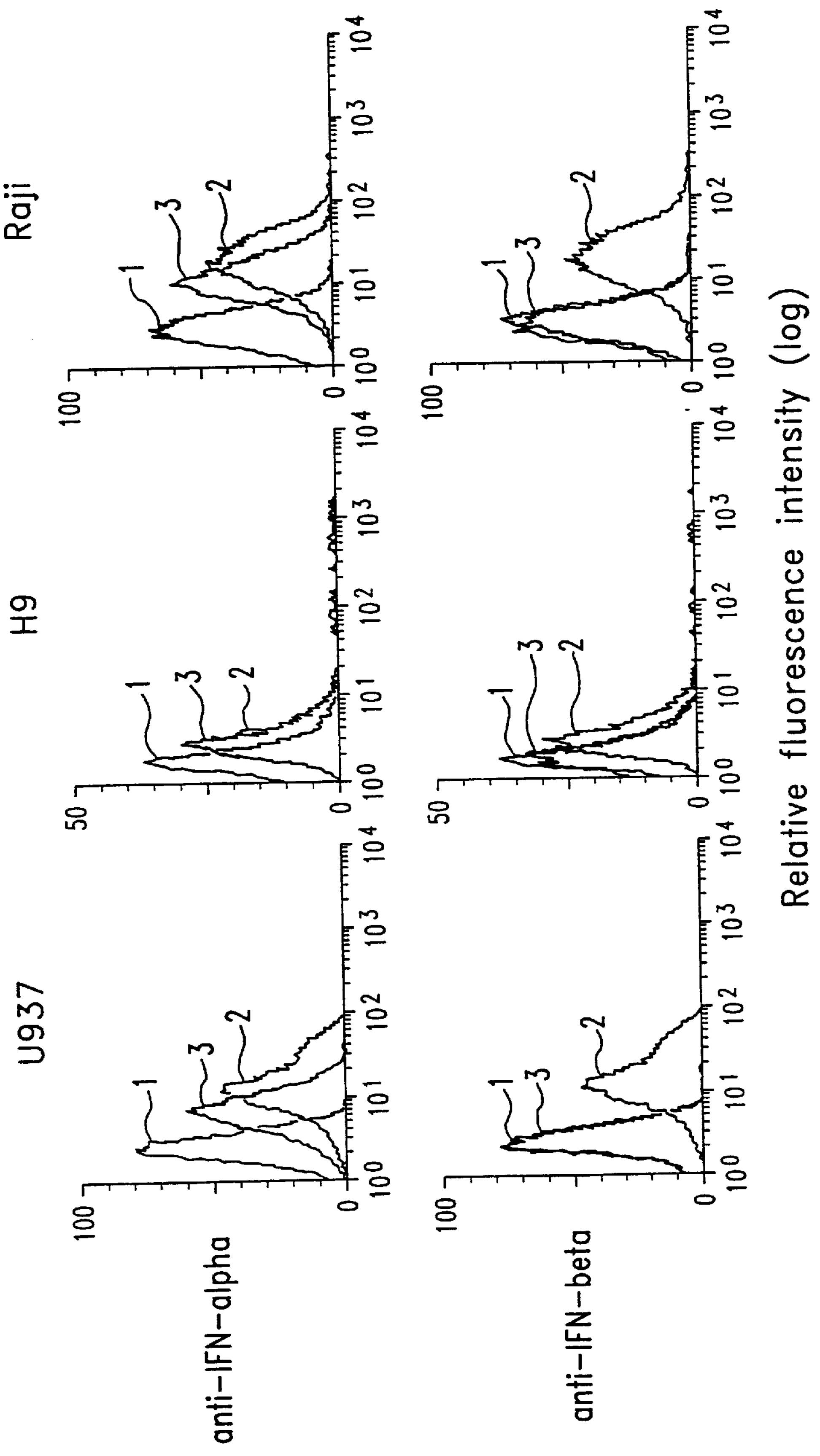
Figure 4B:
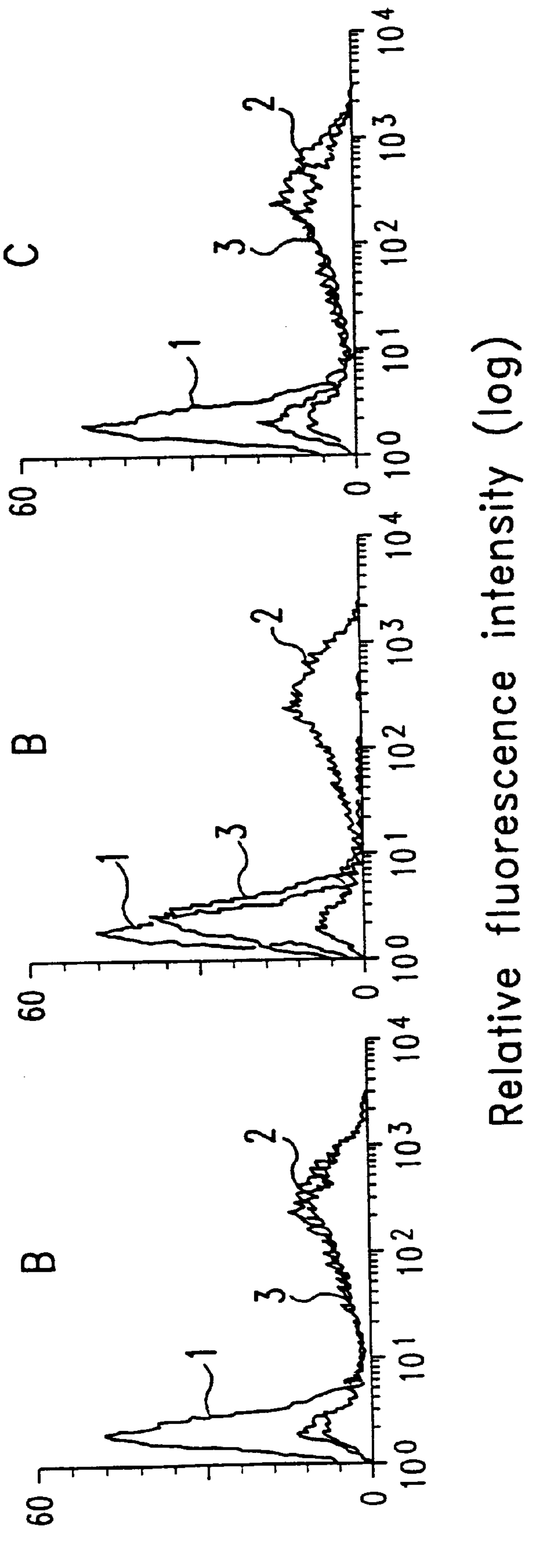

FIG. 4: a, inhibition of rsgp41 binding to human monocyte cell line U937, T cell line H9 and B cell line Raji by polyclonal sheep antibodies (immunoglobulin) to human IFN-Á and IFN-β in immunofluorescence assay; b. inhibition of rsgp41 binding to U937 by control antibody (normal sheep immunoglobulin)

A, inhibition by sheep anti-huIFN-α antibody; B, inhibition by sheep anti-huIFN-β antibody; C, inhibition by normal sheep immunoglobulin. FACS-histogram overlays: (1) FITC-conjugated Streptavidin (control) (1:50); (2) preincubation of biotinylated rsgp41 (100 ng in 25 μl PBS) with 25 μl PBS for 15 min, then plus FITC-conjugated Streptavidin; (3) preincubation of biotinylated rsgp41 (100 ng) with 25 μl anti-IFN-β antibody (1x$10^3$NU/ml) or with 25 μl normal sheep immunoglobulin (20 μg/ml), then plus FITC-conjugated Streptavidin.

Figure 5:
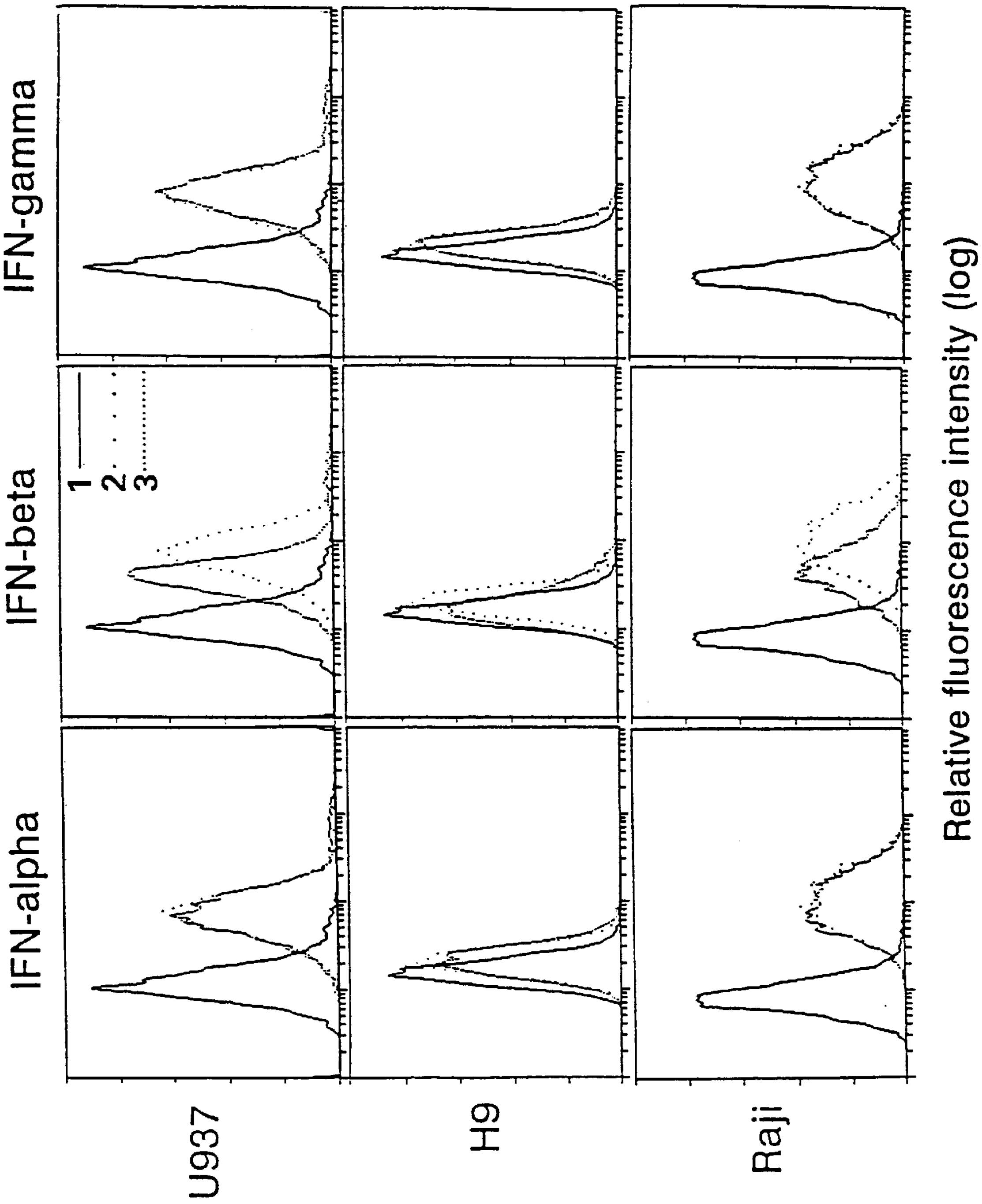

FIG. 5: Inhibition of rsgp41 binding to human cell lines U937, H9 and Raji by human IFN-Á, -β and -c in immunofluorescence assay FACS-histogram overlays: (1) FITC-conjugated Streptavidin (control) (1:50); (2) biotinylated-rsgp41 (100 ng) plus FITC-conjugated Streptavidin; (3) preincubation of cells with IFN-α, or -β and -c (2x$10^4$ U/ml), then plus biotinylated rsgp41 (100 ng) and FITC-conjugated Streptavidin.

Figure 6:
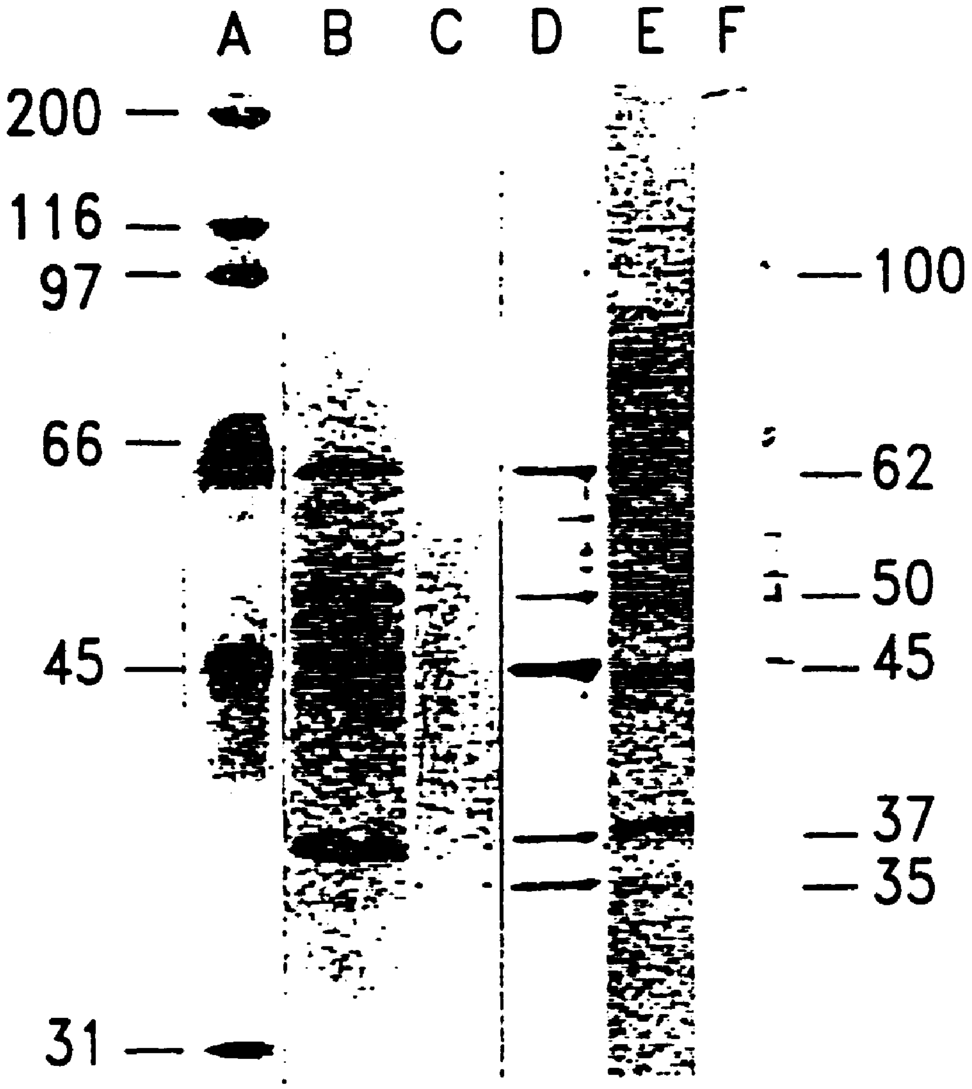

FIG. 6: Identification of rsgp41 and IFN-β binding proteins in Raji cell solutes by Coomassie Blue staining Raji cell solutes passed through rsgp41, and/or IFN-β sepharose columns (in control, through BSA-column). Eluates were analysed by SDS-PAGE (9.5% gel) under non-reducing conditions. A, molecular weight markers; B, rsgp41-eluate; C, BSA-eluate; D, rsgp41-eluate; E, IFN-β-eluate; F, rsgp41/IFN-β-eluate (rsgp41-eluate passed through IFN-β column). (Each lane represents an eluate of 1x$10^8$ cells).

Figure 7:
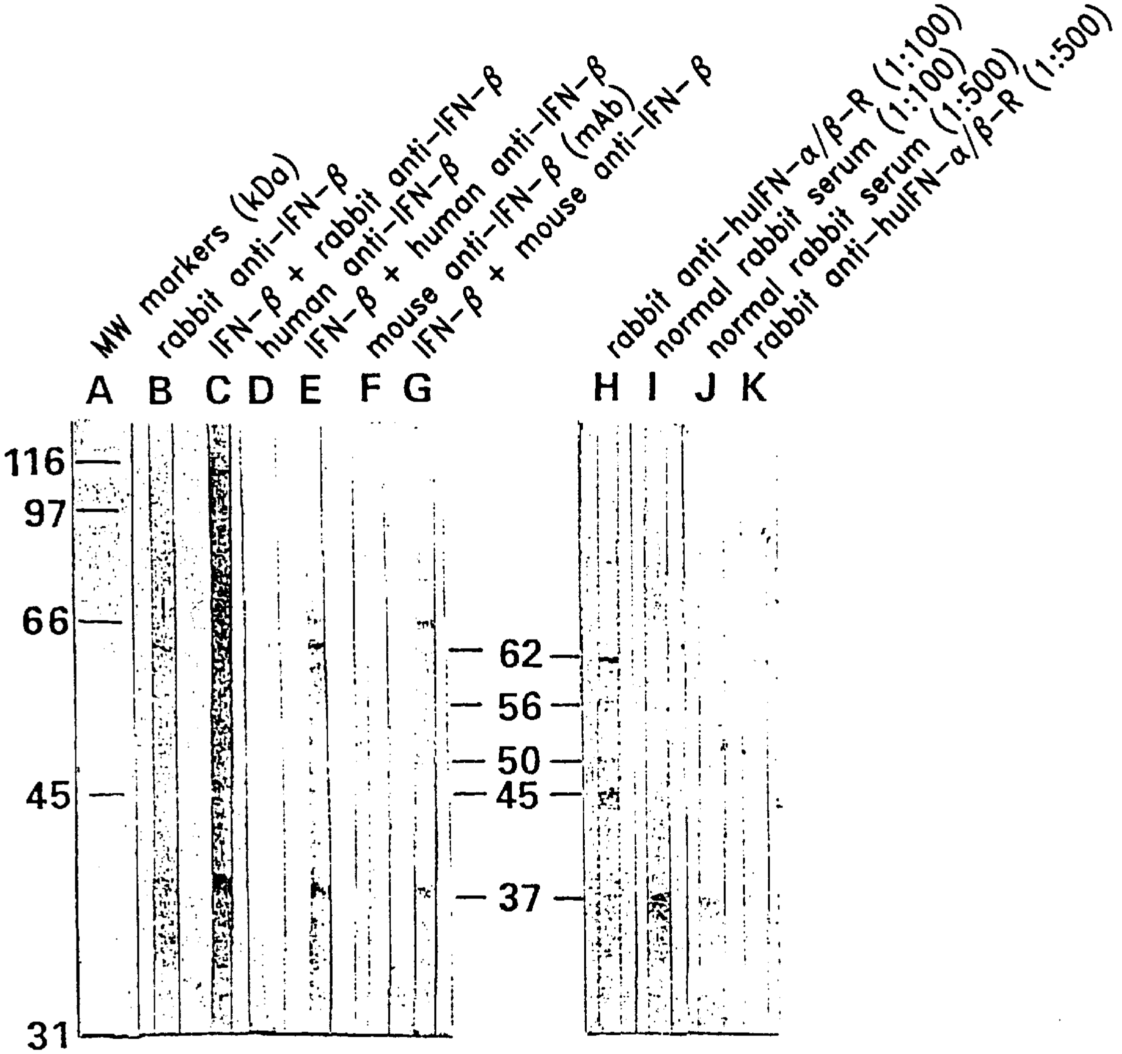

FIG. 7: Identification of human IFN-β binding proteins in rsgp41 eluate by Western blot Rsgp41 eluates from Raji cell solutes were subjected to SDS-PAGE (9.5% gel) under non-reducing condition and blotted using IFN-β (1.5x$10^6$ U/ml) and three different anti-huIFN-β antibodies (from rabbit, human and mouse) (lane C, E, G), or using rabbit anti-human IFN-α/β receptor antiserum (lane H, K). Lane B, D, F, I and J are controls (without IFN-β or anti-IFN-α/β-receptor).

Figure 8:
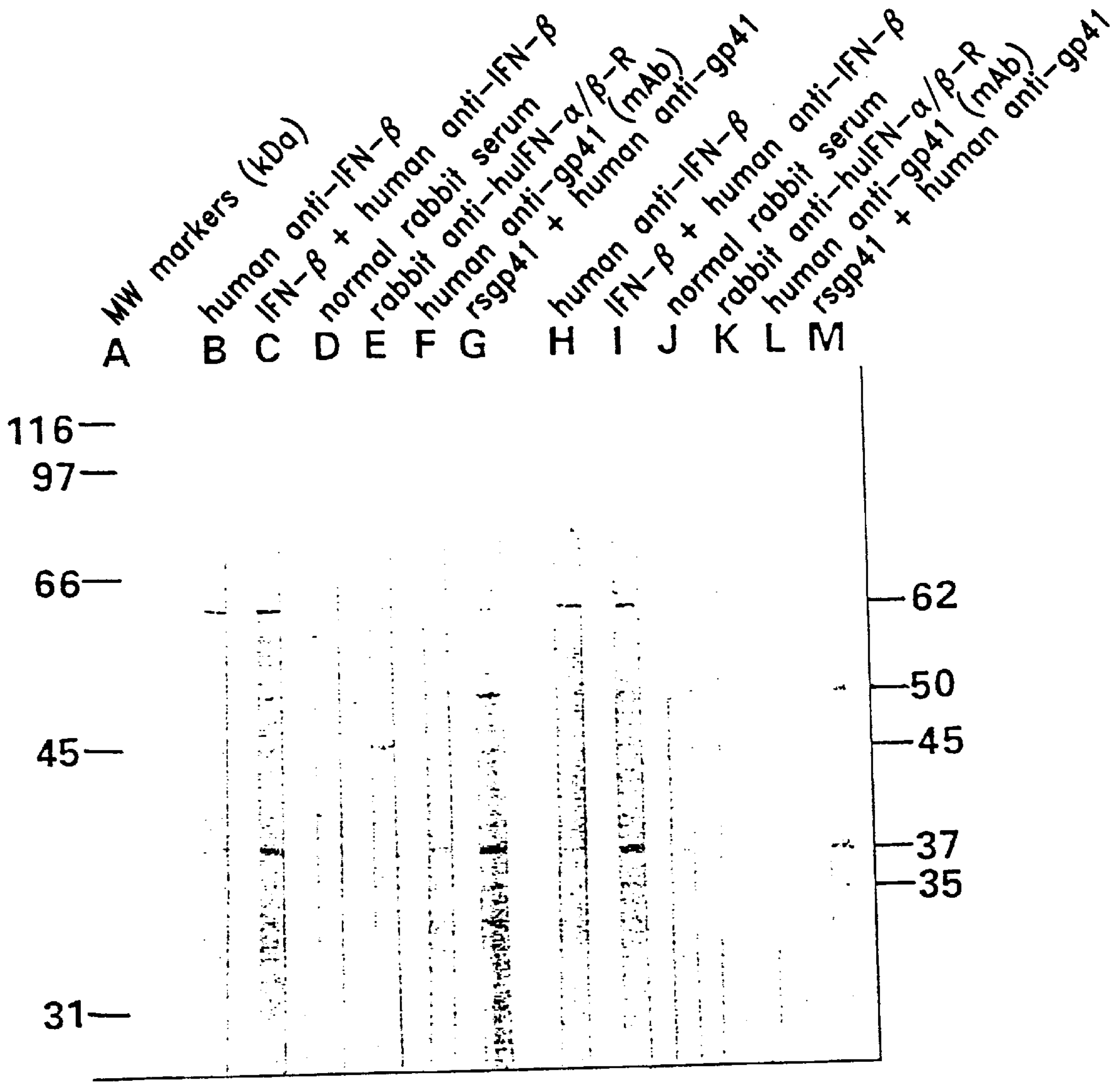

FIG. 8: Identification of common cellular proteins in rsgp41 and IFN-β eluates for binding of rsgp41, IFN-β and anti-IFN-β -receptor antibody by Western blot.

IFN-β eluate and rsgp41/IFN-β eluate from Raji cell solutes were subjected to SDS-PAGE (9.5% gel) under reducing condition and blotted using IFN-β ($1.5 \times 10^6$ U/ml) plus human anti-huIFN-β antibodies (lane, C, I), or using rabbit anti-human IFN-α/β receptor antiserum (lane E, K), or using rsgp41 plus human anti-gp41 antibody 4BE (lane G, M). Lane B, D, F, H, J and L are controls (without IFN-β or anti-IFN-α/β-receptor and rsgp41). Lanes B–G represented IFN-β eluate and lanes H–M represented rsgp41/IFN-β eluate.

Figure 9:
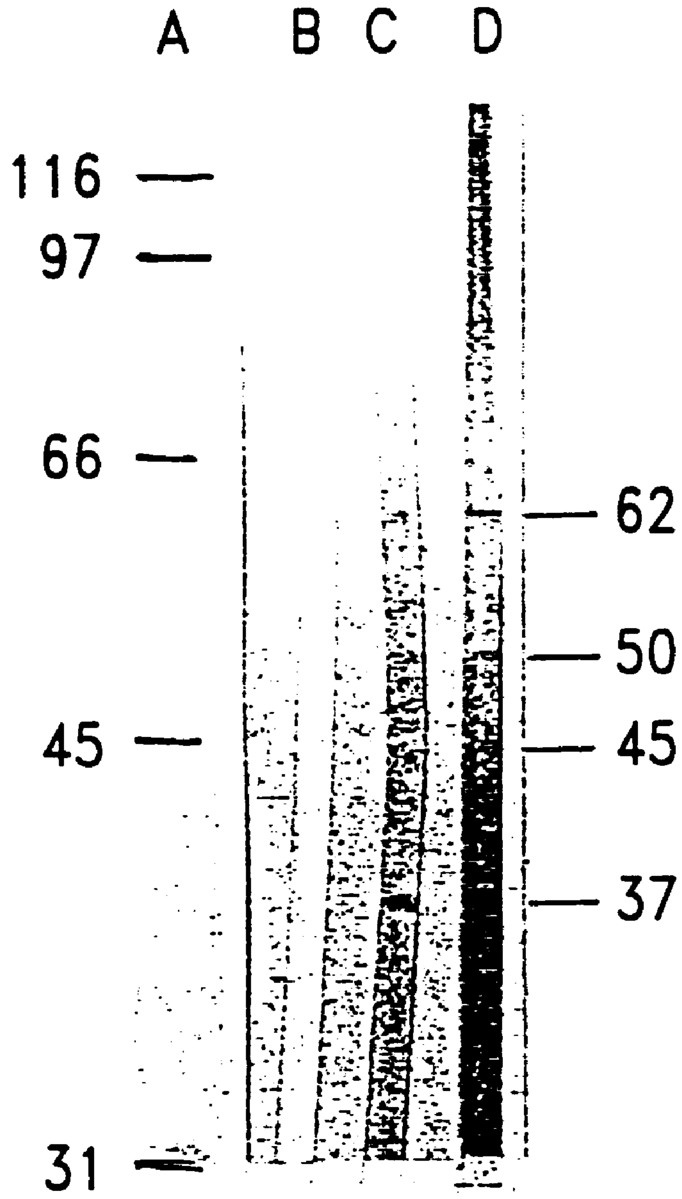

FIG. 9: Rsgp41 from two different sources can bind to human IFN-β binding proteins in IFN-β-eluate by Western blot.

IFN-β eluate was subjected to SDS-PAGE (9,5% gel) under reducing conditions and blotted using the following probes: lane A, molecular weight markers; lane B, mAb 4B3 control (without rsgp41); lane C, rsgp41 (Biotest) plus human anti-gp41 antibody 4B3 (mAb); lane D, rsgp41 (NEN) plus antibody 4B3.

Figure 10:
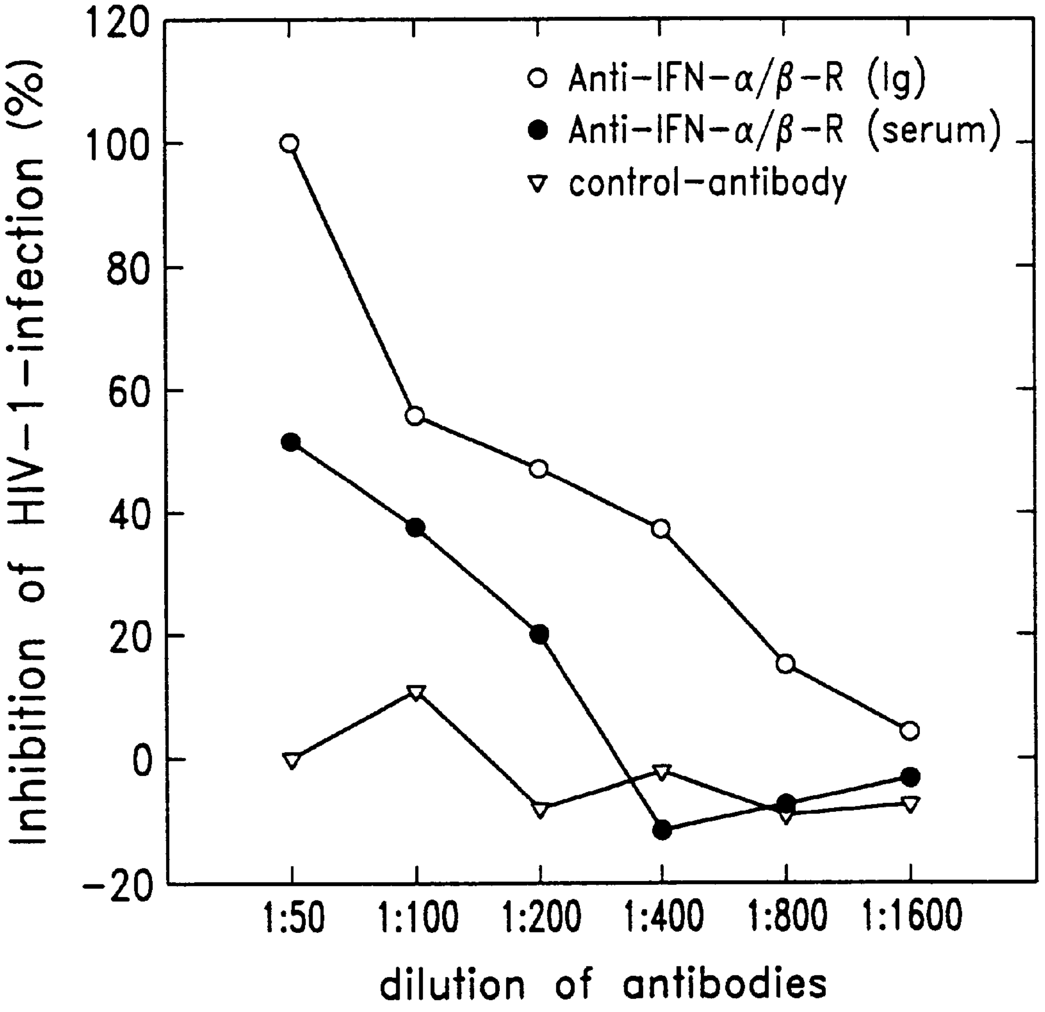

FIG. 10: Inhibition of HIV-infection of human PBMC by rabbit anti-human-IFN-Á/β-receptor Polyclonal antibodies (purified immunoglobulins) and antiserum as well as a control antibody (purified normal rabbit immunoglobulins).

P24-production tested in p24-ELISA was used as virus replication marker. The concentrations of purified rabbit immunoglobulins are 100 μg/ml. A 1:50 dilution corresponds to 2 μg/ml Ig.

The following examples illustrate the invention:

EXAMPLE 1

Anti-IFN-β-antibody recognised rsgp41 and gp41-ISP-region aa583–599, the immunosuppressive domain of HIV-1 gp41, and aa655–675 mediate binding of gp41 to human cells (Chen et al., AIDS 6 (1992), 533–539; Qureshi et al., AIDS 4 (1990), 553–558; Henderson and Qureshi, J. Biol. Chem. 268 (1993), 15291–15297). Based on the finding that gp41 showed similar effects as human IFN-α and -β, but not -c, on the regulation of MHC molecule expression and the inhibition of lymphoproliferation the amino acid sequence of HIV-1 gp41 was compared with human interferons. It was found that aa586–596 showed sequence similarity with two regions in human IFN-α and -β (aa29–35 and 123–140), which had been reported to form IFN-α/β receptor binding domains (Fish, J. Interfer. Res. 12 (1992), 257–266, and Fish et al., ibida 9 (1989), 97–114). Sequence comparison showed a common three-amino acids epitope (LKD) existing in gp41 (aa594–596) and in the first IFN-α/β receptor binding region of IFN-α and β (aa29–35) (FIG. 1-A); in addition, aa581–600 of gp41 showed several amino acids identical with those of the second IFN-α/β receptor binding region in IFN-β (aa123–140) and in IFN-α (aa117–129) (FIG. 1-B). The second binding site in gp41 (aa655–675) did not show sequence similarity with human IFN-α and IFN-β.

Based on the fact that there is a common amino acid sequence between receptor binding sites in gp41 and in IFN-α and IFN-β, it was examined whether anti-IFN-α or anti-IFN-β antibodies (polyclonal) can recognise aa539–684 or rsgp41 and gp41 IS-peptide (aa583–599).

Rsgp41 from Biotest (Dreieich, Germany), represents the external portion of the transmembrane protein gp41 of HIV-1 (derived from clone BH10). The soluble transmembrane proteins were expressed in E. coli and purified. The relative molecular weight of rsgp41 was 18 kD. The binding of the recombinant proteins to CNBr-Sepharose CL 4B (Pharmacia) was performed at a concentration of 1 mg/ml sepharose. Using the Biotin-X-NHS Kit (Calbiochem, No.: 813193; California) and the biotinylation-method as suggested by Calbiochem, rsgp41 was biotin-labeled. HIV-1 gp41 peptide aa567–648 (rsgp41-NEN) was obtained from NEN (DuPont NEN, No.: NEA-211). The gp41 immunosuppressive peptide was synthesized according to the sequence of the HIV-1 isolate IIIB: HIV aa583–599, LQARILAVERYLKDQQL (SEQ ID NO:1). P2 is a gp41 peptide containing the second cellular binding site (Chen et al., AIDS 6 (1992), 533–539): HIV-$1_{IIIB}$ Env aa654–677, EESQNQQEKNEQELLELDKWASLW (SEQ ID NO:6). CP is a control peptide with the sequence KDPDAEDASNIMRVISIK (SEQ ID NO:7), obtained from A. Eberhald (Institute for Biochemical Pharmacology, University Innsbruck, Austria).

Human antiserum (pool) to human IFN-β, rabbit polyclonal and mouse monoclonal anti-human IFN-β antibodies were obtained from Rentschler Biotechnology (Germany). Mouse monoclonal (AB-20–050) and sheep polyclonal (Ab-19–105) were obtained from Biosource International (California, USA). Human mAb to HIV-1 gp41 (4B3) was obtained from Dr. H. Katinger (Institute of Applied Microbiology, Vienna, Austria). Peroxidase-conjugated rabbit immunoglobulines to mouse immunoglobulines (P161) and to human immunoglobulines (P214), peroxidase-conjugated swine immunoglobulines to rabbit immunoglobulins (P217) and FITC-conjugated Streptavidin (F422) were obtained from Dako (Vienna, Austria). Rabbit polyclonal anti-human IFN-α/β receptor antibody was provided by Dr. D. Novick (Weizmann Institute of Science, Israel).

The sheep anti-human-IFN-β antibody (polyclonal) dose-dependently could bind to rsgp41 in an ELISA-assay (FIG. 2, B); the sheep anti-human-IFN-α antibody (polyclonal) could bind less well (FIG. 2, A); two control antibodies (Ab1: sheep immunoglobulin to human factor I: Ab2: normal sheep immunoglobulin) showed background values (FIG. 2, C). The sheep anti-IFN-β antibody could recognise two types of rsgp41 (aa539–684 and aa567–684) from two different sources (Biotest, Germany; Du Pont NEN, USA) (FIG. 3, B), and bind weakly to monomeric gp41 IS-peptide (ISP, aa583–599), but better to ISP conjugated to BSA (ISP-BSA). It could neither bind to gp41 peptide P2 (aa654–677) and a control peptide (CP) nor to their BSA-conjugates (P2-BSA; CP-BSA) and EDC-treated carrier protein (BSA/EDC) (FIG. 3, A). (Conjugation was carried out with globulin-free BSA (Sigma, No. A.7638) using EDC (Sigma, No. E-6383) according to Colgan et al., Current Protocols In Immunology, published by John Wiley and Sons, Inc. USA (1991), 9.3.4. Peptide-protein conjugates were extensively dialysed against phosphate-buffered saline (PBS) before use).

EXAMPLE 2

Anti-IFN-β antibody and human IFN-β block binding of rsgp41 to various target cells U937 is a human monocyte cell line; H9, a $CD4^+$ human T cell line; Raji, a human B cell line. These cell lines were grown in RPMI 1640 medium supplemented with 10% fetal calf serum (FCS), 2 mmol/l glutamin, 100 IU/ml penicillin and 100 μg/ml streptomycin. Since rsgp41 has been shown to bind strongly to human monocyte cell line U937 and B cell line Raji and weakly to human $CD4^+$ T cell line H9 it was examined whether the anti-IFN-α or -β antibodies could block rsgp41 binding to U937, Raji and H9. The results demonstrate that the anti-IFN-β antibody, if preincubated with rsgp41, could completely inhibit rsgp41 binding to U937, Raji and H9; the anti-IFN-α antibody showed only a partial blockade (FIG. 4, A); in control, normal sheep immunoglobulin like anti-IFN-α antibody showed also a partial inhibition of rsgp41 binding to U937 (FIG. 4, B).

Since the anti-IFN-β antibody could strongly inhibit rsgp41 binding to U937, Raji and H9 cells and IFN-β had considerable sequence homology with gp41, it was examined whether human IFN-β could inhibit rsgp41 binding to these cells by blocking of IFN-α/β-receptors on the cell surface. The results demonstrated that human IFN-β at a dose of $2\times10^6$ U/ml, if preincubated with U937, or Raji and H9 cells, could partially inhibit rsgp41 binding to the cells, while human IFN-α and c, could not at all influence binding (FIG. 5), showing that inhibition by IFN-β is highly specific.

EXAMPLE 3

Human IFN-β and HIV-1 share common cellular binding proteins

Since the anti-IFN-β antibody could strongly inhibit rsgp41 binding to U937, Raji and H9 cells and IFN-β had considerable sequence homology with gp41, it was examined whether human IFN-β could inhibit rsgp41 binding to these cells by blocking of IFN-α/β-receptors on the cell surface. The results demonstrated that human IFN-β at a dose of $2\times10^6$ U/ml, if preincubated with U937, or Raji and H9 cells, could partially inhibit rsgp41 binding to the cells while human IFN-α and IFN-c could not at all influence the binding (FIG. 5).

Several cellular binding protein for HIV-1 gp41 were identified in cell solutes of human T, B and monocyte cells in three laboratories (Chen et al., AIDS 6 (1992), 533–539; Chen et al., Mol. Immunol. 30(1993), 1159–1163; Chen et al., Immunol. Letters 37 (1993), 41–45; Ebenbichler et al., AIDS 7 (1993), 489–495; Qureshi et al., AIDS 4 (1990), 553–558; Henderson et al., J. Biol. Chem. 268 (1993), 15291–15297 and Denner et al., J. Can. Res. Clin. Oncol. 121 (S1) (1995), 535 (11/128). To examine whether IFN-β could recognise similar cellular proteins Raji cell solutes were passed through a human IFN-β-sepharose column. The procedure of protein-coupling to sepharose, cell soluble preparation and adsorption was carried out as described in Chen et al., Mol. Immunol. 30 (1993), 1159–1163. Four protein bands of 37, 45, 50 and 62 kDa were always observed in gp41-eluates by Coomassie blue staining (FIG. 6, lane B and D); sometimes, a few faint bands of 35, 52–60, 80 and 90–100 kDa were seen (FIG. 6, lane D). The eluate from a human IFN-β-sepharose column showed a similar banding pattern with bands at 37, 45, 50 and 62 kDa (FIG. 6, lane E). To examine whether IFN-β binding proteins were identical with gp41 binding proteins, gp41 eluate from Raji-solute was adsorbed to and eluated from IFN-β-sepharose column. This eluate contained the same binding proteins as a gp41 eluate (FIG. 6, lane F). In eluates from Raji-solutes passed through a BSA-sepharose column, no protein band was seen (FIG. 6, lane C).

EXAMPLE 4

Human IFN-β as well as anti-human IFN-Á/β-receptor antibody recognised gp41-binding proteins by Western blot To further elucidate whether gp41 binding proteins and IFN-β binding proteins were identical it was examined whether anti-human IFN-α/β receptor antibody and human IFN-β recognised gp41-binding proteins in gp41-eluate from Raji cell solutes by Western blot analysis after electrophoresis in 9.5% SDS-PAGE under non-reducing conditions. Before probing, blots were blocked in PBS supplemented with 0.1% gelatine, 1% dried milk, 0.05% Tween-20. Binding of rabbit anti-human IFN-α/β receptor antibody was detected with peroxidase-conjugated swine-anti-rabbit IgG (1:100 and 1:500). Normal rabbit serum instead rabbit anti-IFN-α/β receptor antibody was used as negative control. Four proteins bands of 45, 50, 57 and 60 kDa were identified in rsgp41-eluate by rabbit anti-human IFN-α/β receptor antiserum (FIG. 7, lane H and K), the 37 kDa band was detected very weakly by using the anti-receptor antiserum, and strongly by a normal rabbit serum (control) (FIG. 7, lane I and J). By ligand blot analysis using IFN-β and three different antibodies (from human, rabbit and mouse) to human IFN-β, four similar or identical bands of 45, 50, 57 and 60 kDa were blotted (FIG. 7, lane C, E and G). The 57 and 60 kDa band are faint, the binding to bands of 37 and 62 kDa was strong, while the rabbit and human (but not mouse mAb, FIG. 7, lane F) antisera to IFN-β alone could weakly bind to these (FIG. 7, lane B and D). Besides, a few bands of 66, 80 and 100–120 kDa were also observed (FIG. 7, lane C, E and G) with IFN-β and anti-IFN-β antibody.

EXAMPLE 5

Rsgp41, human IFN-β and IFN-Á/β-receptor antibody recognised common cellular proteins by Western blot To further examine whether rsgp41 and IFN-β share cellular binding proteins, we used an IFN-β-eluate (FIG. 8, lanes B–G) from Raji cell solutes (adsorbed by IFN-β-sepharose column) for Western blot or ligand blot analysis using rsgp41, IFN-β and IFN-α/β-receptor antibody. Human IFN-β, the anti-human IFN-α/β-receptor antibody and rsgp41 bound to the same proteins of 45 and 50 kDa in both eluates (FIG. 8, lane C, E, G, I, K and M); in controls (without IFN-β, or rsgp41 and IFN-α/α-R antibody), both proteins were not seen (FIG. 8, lane B, D, F, H, J and L). The binding to the bands of 37 and 62 kDa was strong. In controls, the human antiserum could bind strongly to 62 kDa and weakly to 37 kDa protein (FIG. 8, lane B and H) and normal rabbit serum and human mAb could weakly bind to 37 kDa protein.

EXAMPLE 6

RSGP41 (from Biotest or NEN) binds to IFN-β-binding-proteins

The binding of rsgp41 from two different sources to IFN-β binding proteins was examined. The results demonstrated that rsgp41 from Biotest or NEN showed identical binding specifity as IFN-β, namely, rsgp41 could bind the same proteins of 37, 45, 50 and 62 kDa from IFN-β-eluate (FIG. 9, lane C and D), while the human anti-gp41 antibody alone did not (lane B).

EXAMPLE 7

Anti-human-IFN-Á/β-receptor-antibodies inhibited HIV-infection of PBMC

It was examined whether anti-human-IFN-α/β receptor antibodies could inhibit HIV-infection of human PBMC. PBMC from healthy HIV-seronegative blood donors were infected with HIV-$1_{IIIB}$. P24-production tested in p24-ELISA was used as virus replication marker (Purtscher et al., AIDS Res. Hum. Retroviruses 10 (1994), 1651–1658). The virus titer was determined by measuring p24 in the supernatant. The assay was performed with 4 replicates and repeated three times. The results showed that the rabbit anti-human-IFN-α/β-receptor polyclonal antibodies (purified immunoglobulins, sc-704, Santa Cruz Biotechnology, Inc.; California, USA) and polyclonal antiserum (obtained from Dr. D. Novick, Weizmann Institute of Science, Israel) could inhibit HIV-$1_{IIIB}$-infection of human PBMC; the inhibition by purified antibodies is stronger than by the antiserum, while purified normal rabbit immunoglobulins as control antibody did not inhibit HIV-infection (FIG. 10). Normal rabbit serum did not show any inhibition (data not shown).

SEQUENCE LISTING

```
<160> NUMBER OF SEQ ID NOS: 7

<210> SEQ ID NO 1
<211> LENGTH: 17
<212> TYPE: PRT
<213> ORGANISM: Artificial Sequence
<220> FEATURE:
<223> OTHER INFORMATION: Source of Artificial Sequence: synthesized
      according to the sequence of the the HIV-1 isolate
      IIIB (aa 583-599)

<400> SEQUENCE: 1

Leu Gln Ala Arg Ile Leu Ala Val Glu Arg Tyr Leu Lys Asp Gln Gln
  1               5                  10                  15

Leu


<210> SEQ ID NO 2
<211> LENGTH: 7
<212> TYPE: PRT
<213> ORGANISM: Artificial Sequence
<220> FEATURE:
<223> OTHER INFORMATION: Source  of Artificial Sequence: synthesized
      according to the receptor binding region 1 of
      human IFN-alpha (aa29-35.)

<400> SEQUENCE: 2

Cys Leu Lys Asp Arg His Asp
  1               5


<210> SEQ ID NO 3
<211> LENGTH: 7
<212> TYPE: PRT
<213> ORGANISM: Artificial Sequence
<220> FEATURE:
<223> OTHER INFORMATION: Source of Artificial Sequence: synthesized from
      receptor binding region 1 of human IFN-beta (aa
      29-35)

<400> SEQUENCE: 3

Cys Leu Lys Asp Arg Met Asn
  1               5


<210> SEQ ID NO 4
<211> LENGTH: 14
<212> TYPE: PRT
<213> ORGANISM: Artificial Sequence
<220> FEATURE:
<223> OTHER INFORMATION: Source of Artificial Sequence: synthesized from
      the human IFN-alpha receptor binding region 2 (aa
      123-140)

<400> SEQUENCE: 4

Ser Ile Leu Ala Val Arg Lys Tyr Phe Gln Arg Ile Thr Leu
  1               5                  10


<210> SEQ ID NO 5
<211> LENGTH: 18
```

-continued

```
<212> TYPE: PRT
<213> ORGANISM: Artificial Sequence
<220> FEATURE:
<223> OTHER INFORMATION: Source of Artificial Sequence: synthesized from
      the human IFN-beta receptor binding region 2
      (aa123-140)

<400> SEQUENCE: 5

Tyr Tyr Gly Arg Ile Leu His Tyr Leu Lys Ala Lys Glu Tyr Ser His
  1               5                  10                  15

Cys Ala


<210> SEQ ID NO 6
<211> LENGTH: 24
<212> TYPE: PRT
<213> ORGANISM: Artificial Sequence
<220> FEATURE:
<223> OTHER INFORMATION: Source of Artificial Sequence: synthesized from
      the HIV-1 IIIB Env protein (aa 654-677)

<400> SEQUENCE: 6

Glu Glu Ser Gln Asn Gln Gln Glu Lys Asn Glu Gln Glu Leu Leu Glu
  1               5                  10                  15

Leu Asp Lys Trp Ala Ser Leu Trp
             20


<210> SEQ ID NO 7
<211> LENGTH: 18
<212> TYPE: PRT
<213> ORGANISM: Artificial Sequence
<220> FEATURE:
<223> OTHER INFORMATION: Source of Artificial Sequence: synthesized
      control peptide with no function or intended sequence
      identity

<400> SEQUENCE: 7

Lys Asp Pro Asp Ala Glu Asp Ala Ser Asn Ile Met Arg Val Ile Ser
  1               5                  10                  15

Ile Lys
```

What is claimed is:

1. Pharmaceutical composition comprising a protein, peptide or a functionally equivalent molecule or a combination thereof with the exception of interferon and HIV-gp41 which competitively inhibits the binding of a retrovirus to the interferon-(IFN)-receptor of a target cell and optionally a pharmaceutically acceptable carrier.

2. Pharmaceutical composition according to claim 1 wherein the receptor is the IFN-α/β-receptor.

3. Pharmaceutical composition according to claim 1, wherein the retrovirus is HIV.

4. Pharmaceutical composition according to claim 2, wherein the protein, peptide or functionally equivalent molecule binds to the IFN-α/β-receptor.

5. Pharmaceutical composition according to claim 4, wherein the protein or peptide is an anti-IFN-α/β-receptor antibody or a fragment of said protein or a peptide containing a HIV-gp41-receptor-binding site (epitope), or a fragment of IFN-α or IFN-β containing the IFN-α/β-receptor-binding site (epitope).

6. Pharmaceutical composition comprising at least 2 proteins or peptides according to claim 4.

7. Pharmaceutical composition according to claim 1 for preventing or treating a retroviral infection.

8. Pharmaceutical composition according to claim 7, wherein the retroviral infection is an HIV infection.

9. Pharmaceutical composition according to claim 1, additionally comprising an anti-retroviral drug.

10. Pharmaceutical composition according to claim 1, further comprising a ligand to CD4, or a ligand to gp120 surface protein of HIV.

11. A method for treatment of a retroviral infection comprising administrating to a patient in need thereof a protein, peptide or a functionally equivalent molecule which competitively inhibits the binding of a retrovirus to the IFN-receptor of a target cell by blocking those domains of the IFN-receptor that are responsible for the binding of a retrovirus or by blocking those domains of the retroviral envelope proteins that are responsible for binding to the IFN-receptor.

12. The method according to claim 11, wherein the receptor is the IFN-α/β-receptor.

13. The method according to claim 11, wherein the retrovirus is HIV.

14. The method according to claim 12, wherein the protein, peptide or functionally equivalent molecule binds to HIV-gp41.

15. The method according to claim 12, wherein the protein, peptide or functionally equivalent molecule binds to the IFN-α/β-receptor.

16. The method according to claim 15, wherein the protein or peptide is HIV-gp41, and anti-IFN-α/β-receptor antibody or a fragment of said protein or peptide containing a HIV-gp41-receptor-binding site (epitope), or IFN-α- or IFN-β- or a fragment thereof containing the IFN-α/β-receptor-binding site (epitope).

17. The method according to claim 14, wherein the protein or peptide is a soluble IFN-α/β-receptor, an anti-IFN-β-antibody, an anti-HIV-gp41-antibody or a fragment of said protein or peptide containing an HIV-gp-41-binding site (epitope).

18. The method according to claim 11, wherein the pharmaceutical composition comprises a ligand to CD4, or a ligand to gp120 surface protein of HIV.

19. The method according to claim 11, wherein the protein, peptide or functionally equivalent molecule is additionally combined with an anti-retroviral drug and/or ligand to CD4.

20. A method for treatment of a retroviral infection comprising administrating to a patient in need thereof a protein, peptide or a functionally equivalent molecule which binds to HIV-gp41 and which competitively inhibits the binding of a retrovirus to the IFN-α/β-receptor of a target cell by blocking those domains of the IFN-α/β-receptor that are responsible for the binding of a retrovirus or by blocking those domains of the retroviral envelope proteins that are responsible for binding to the IFN-α/β-receptor.

21. A method for treatment of a retroviral infection comprising administrating to a patient in need thereof a protein, peptide or a functionally equivalent molecule which binds to HIV-gp41 and which competitively inhibits the binding of a retrovirus to the IFN-α/β-receptor of a target cell by blocking those domains of the IFN-α/β-receptor that are responsible for the binding of a retrovirus or by blocking those domains of the retroviral envelope proteins that are responsible for binding to the IFN-α/β-receptor, wherein said protein, peptide or functionally equivalent molecule is a soluble molecule selected from the group consisting of the IFN-α/β-receptor, an anti-IFN-α/β-receptor, an anti-HIV-gp41-antibody and a fragment of said protein that contains an HIV-gp41-binding site (epitope).

22. A method of treatment comprising administering to a patient in need thereof an effective amount of a pharmaceutical composition comprising a protein, peptide or a functionally equivalent molecule or a combination thereof with the exception of interferon and HIV-gp41, which competitively inhibits the binding of a retrovirus to the interferon-(IFN)-receptor of a target cell and optionally a pharmaceutically acceptable carrier.

23. The method according to claim 22, wherein the receptor is the IFN-α/β-receptor.

24. The method according to claim 22, wherein the retrovirus is HIV.

25. The method according to claim 23, wherein the protein, peptide or functionally equivalent molecule binds to the IFN-α/β-receptor.

26. The method according to claim 25, wherein the protein or peptide is an anti-IFN-α/β-receptor antibody or a fragment of said protein or a peptide containing a HIV-gp41-receptor-binding site (epitope), or a fragment of IFN-α or IFN-β containing the IFN-α/β-receptor-binding site (epitope).

27. The method according to claim 25, wherein said pharmaceutical composition comprises at least two proteins or peptides and wherein said proteins bind to the IFN-α/β-receptor.

28. The method according to claim 22, wherein the pharmaceutical composition additionally comprises and anti-retroviral drug.

29. The method according to claim 22, wherein the pharmaceutical composition further comprises a ligand to CD4, or a ligand to gp120 surface protein of HIV.

30. A method for inhibiting or treating a retroviral infection comprising administrating to a patient in need thereof a protein, peptide or a functionally equivalent molecule or combination thereof, with the exception of IFN-α, which binds to HIV-gp41 and which competitively inhibits the binding of a retrovirus to the IFN-α/β-receptor of a target cell by blocking those domains of the IFN-α/β-receptor that are responsible for the binding of a retrovirus or by blocking those domains of the retroviral envelope proteins that are responsible for binding to the IFN-α/β-receptor.

* * * * *